United States Patent
Fazio et al.

(10) Patent No.: US 9,150,627 B2
(45) Date of Patent: Oct. 6, 2015

(54) ANTI TUMORAL IMMUNOGENIC PEPTIDES AND VACCINE THEREOF

(75) Inventors: Vito M. Fazio, Rome (IT); Enrico Garaci, Rome (IT); Guido Rasi, Rome (IT); Monica Rinaldi, Rome (IT); Paola Sinibaldi, Rome (IT)

(73) Assignees: Vito Michele Fazio, Rome (IT); Enrico Garaci, Rome (IT); Monica Rinaldi, Rome (IT); Paola Sinibaldi, Rome (IT)

( * ) Notice: Subject to any disclaimer, the term of this patent is extended or adjusted under 35 U.S.C. 154(b) by 1751 days.

(21) Appl. No.: 11/722,863

(22) PCT Filed: Dec. 29, 2005

(86) PCT No.: PCT/IT2005/000780
§ 371 (c)(1),
(2), (4) Date: Nov. 20, 2008

(87) PCT Pub. No.: WO2006/070432
PCT Pub. Date: Jul. 6, 2006

(65) Prior Publication Data
US 2009/0232837 A1  Sep. 17, 2009

(30) Foreign Application Priority Data

Dec. 30, 2004 (GB) .................................. 0428525.0
Mar. 18, 2005 (IT) ............................. RM2005A0128

(51) Int. Cl.
C07K 4/00 (2006.01)
C07H 21/02 (2006.01)
C07K 14/47 (2006.01)

(52) U.S. Cl.
CPC ..................................... *C07K 14/47* (2013.01)

(58) Field of Classification Search
None
See application file for complete search history.

(56) References Cited

U.S. PATENT DOCUMENTS

2004/0014053 A1* 1/2004 Zerhusen et al. ................. 435/6

FOREIGN PATENT DOCUMENTS

| WO | 9815282 | | 4/1998 |
|---|---|---|---|
| WO | WO 99/64608 | * | 6/1999 |
| WO | 9964608 | | 12/1999 |
| WO | 0001458 | | 1/2000 |
| WO | 0162786 | | 8/2001 |
| WO | 03011908 | | 2/2003 |
| WO | 03045997 | | 6/2003 |
| WO | WO 2004/005458 | * | 1/2004 |
| WO | WO 2004/005458 A2 | * | 1/2004 |

OTHER PUBLICATIONS

Rice et al Feb. 2008 vol. 8 pp. 108-120.*
Wu et al 2003 Cancer Research 63 pp. 8318-8322.*
Yan et al Journal of Biological Chemistry vol. 274 No. 21 Issue May 21 pp. 14926-14935.*
Jaillon et al (Nature, 2004, 431(21): 946-957).*
"Corin-Mediated Processing of Pro-Arterial Natriuretic Peptide in Human Small Cell Lung Cancer Cells." Wu and Wu, 2003. Cancer Research 63: 8318-8322.
"Expression of Wnt ligands and Frizzled Receptors in Colonic Mucosa and in Colon Carcinoma." Holcombe, et al., 2002. Molecular Pathology 55: 220-226.
"GeneCard for Protein-coding CORIN"—http://genome-www.stanford.edu/cgi-bin/genecards/carddisp?CORIN.
"Corin, a Mosaic Transmembrane Serine Protease Encoded by a Novel cDNA from Human Heart" Yan et al. Journal of Biological Chemistry 274:14926-14935, 1999.

* cited by examiner

*Primary Examiner* — Sean Aeder
(74) *Attorney, Agent, or Firm* — Arent Fox LLP

(57) ABSTRACT

The invention relates to novel, Frizzled-like, immunogenic peptides, useful for the stimulation of an immune response against various cancer types, particularly colon rectal carcinoma.

5 Claims, 7 Drawing Sheets

SEQUENCE LISTING

```
<160> NUMBER OF SEQ ID NOS: 43

<210> SEQ ID NO 1
<211> LENGTH: 6
<212> TYPE: PRT
<213> ORGANISM: Unknown
<220> FEATURE:
<223> OTHER INFORMATION: Description of Unknown: Mammalian
      peptide

<400> SEQUENCE: 1

Gln Lys Glu Ala Ser Ile
1               5

<210> SEQ ID NO 2
<211> LENGTH: 8
<212> TYPE: PRT
<213> ORGANISM: Unknown
<220> FEATURE:
<223> OTHER INFORMATION: Description of Unknown: Mammalian
      peptide

<400> SEQUENCE: 2

Arg Thr Gln Lys Glu Ala Ser Ile
1               5

<210> SEQ ID NO 3
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 3

His Arg Thr Gln Lys Glu Ala Ser Ile
```

-continued

```
1               5

<210> SEQ ID NO 4
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 4

Arg Thr Gln Lys Glu Ala Ser Ile Cys
1               5

<210> SEQ ID NO 5
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 5

His Met Thr Gln Lys Glu Ala Ser Ile
1               5

<210> SEQ ID NO 6
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 6

His Arg Glu Gln Lys Glu Ala Ser Ile
1               5

<210> SEQ ID NO 7
<211> LENGTH: 8
<212> TYPE: PRT
<213> ORGANISM: Unknown
<220> FEATURE:
<223> OTHER INFORMATION: Description of Unknown: Mammalian
      peptide

<400> SEQUENCE: 7

Arg Glu Gln Lys Glu Ala Ser Ile
1               5

<210> SEQ ID NO 8
<211> LENGTH: 8
<212> TYPE: PRT
<213> ORGANISM: Unknown
<220> FEATURE:
<223> OTHER INFORMATION: Description of Unknown: Mammalian
      peptide

<400> SEQUENCE: 8

Met Thr Gln Lys Glu Ala Ser Ile
1               5

<210> SEQ ID NO 9
<211> LENGTH: 10
<212> TYPE: PRT
<213> ORGANISM: Unknown
<220> FEATURE:
<223> OTHER INFORMATION: Description of Unknown: Mammalian
``` peptide

<400> SEQUENCE: 9

His Arg Thr Gln Lys Glu Ala Ser Ile Cys
1               5                   10

<210> SEQ ID NO 10
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 10

Met Thr Gln Lys Glu Ala Ser Ile Cys
1               5

<210> SEQ ID NO 11
<211> LENGTH: 9
<212> TYPE: PRT
<213> ORGANISM: Unknown
<220> FEATURE:
<223> OTHER INFORMATION: Description of Unknown: Mammalian
      peptide

<400> SEQUENCE: 11

Arg Glu Gln Lys Glu Ala Ser Ile Cys
1               5

<210> SEQ ID NO 12
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 12

His Met Thr Gln Lys Glu Ala Ser Ile Cys
1               5                   10

<210> SEQ ID NO 13
<211> LENGTH: 10
<212> TYPE: PRT
<213> ORGANISM: Unknown
<220> FEATURE:
<223> OTHER INFORMATION: Description of Unknown: Mammalian
      peptide

<400> SEQUENCE: 13

His Arg Glu Gln Lys Glu Ala Ser Ile Cys
1               5                   10

<210> SEQ ID NO 14
<211> LENGTH: 127
<212> TYPE: PRT
<213> ORGANISM: Homo sapiens

<400> SEQUENCE: 14

Asn Asn Cys Ser Gln Cys Glu Pro Ile Thr Leu Glu Leu Cys Met Asn
1               5                   10                  15

Leu Pro Tyr Asn Ser Thr Ser Tyr Pro Asn Tyr Phe Gly His Arg Thr
            20                  25                  30

Gln Lys Glu Ala Ser Ile Ser Trp Glu Ser Ser Leu Phe Pro Ala Leu
        35                  40                  45

Val Gln Thr Asn Cys Tyr Lys Tyr Leu Met Phe Phe Ser Cys Thr Ile
 50                  55                  60

Leu Val Pro Lys Cys Asp Val Asn Thr Gly Glu Arg Ile Pro Pro Cys
 65                  70                  75                  80

Arg Ala Leu Cys Glu His Ser Lys Glu Arg Cys Glu Ser Val Leu Gly
                 85                  90                  95

Ile Val Gly Leu Gln Trp Pro Glu Asp Thr Asp Cys Ser Gln Phe Pro
                100                 105                 110

Glu Glu Asn Ser Asp Asn Gln Thr Cys Leu Met Pro Asp Glu Tyr
                115                 120                 125

<210> SEQ ID NO 15
<211> LENGTH: 127
<212> TYPE: PRT
<213> ORGANISM: Mus musculus

<400> SEQUENCE: 15

Ser Asn Cys Ser Gln Cys Glu Pro Ile Thr Leu Glu Leu Cys Met Asn
 1               5                  10                  15

Leu Leu Tyr Asn His Thr His Tyr Pro Asn Tyr Leu Gly His Arg Thr
                 20                  25                  30

Gln Lys Glu Ala Ser Ile Ser Trp Glu Ser Ser Leu Phe Pro Ala Leu
             35                  40                  45

Val Gln Thr Asn Cys Tyr Lys Tyr Leu Met Phe Phe Ala Cys Thr Ile
 50                  55                  60

Leu Val Pro Lys Cys Asp Val Asn Thr Gly Gln Arg Ile Pro Pro Cys
 65                  70                  75                  80

Arg Leu Leu Cys Glu His Ser Lys Glu Arg Cys Glu Ser Val Leu Gly
                 85                  90                  95

Ile Val Gly Leu Gln Trp Pro Glu Asp Thr Asp Cys Asn Gln Phe Pro
                100                 105                 110

Glu Glu Ser Ser Asp Asn Gln Thr Cys Leu Leu Pro Asn Glu Asp
                115                 120                 125

<210> SEQ ID NO 16
<211> LENGTH: 127
<212> TYPE: PRT
<213> ORGANISM: Rattus norvegicus

<400> SEQUENCE: 16

Ser Asn Cys Ser His Cys Glu Pro Ile Thr Leu Glu Leu Cys Met Asn
 1               5                  10                  15

Leu Pro Tyr Asn Leu Thr His Tyr Pro Asn Tyr Leu Gly His Arg Thr
                 20                  25                  30

Gln Lys Glu Ala Ser Ile Ser Trp Glu Ser Ala Leu Phe Pro Ala Leu
             35                  40                  45

Val Gln Thr Asn Cys Tyr Lys Tyr Leu Met Phe Phe Ala Cys Thr Ile
 50                  55                  60

Leu Val Pro Lys Cys Asp Val Asn Thr Gly Gln Arg Val Pro Pro Cys
 65                  70                  75                  80

Arg Leu Leu Cys Glu His Ser Lys Glu Arg Cys Glu Ser Val Leu Gly
                 85                  90                  95

Ile Val Gly Leu Gln Trp Pro Glu Asp Thr Asp Cys Ser Gln Phe Pro
                100                 105                 110

Glu Gln Ser Ser Asp Asn Gln Thr Cys Leu Leu Pro Asn Glu Asp
                115                 120                 125

```
<210> SEQ ID NO 17
<211> LENGTH: 125
<212> TYPE: PRT
<213> ORGANISM: Homo sapiens

<400> SEQUENCE: 17

Ala Ser Ala Lys Glu Leu Ala Cys Gln Glu Ile Thr Val Pro Leu Cys
 1               5                  10                  15

Lys Gly Ile Gly Tyr Asn Tyr Thr Tyr Met Pro Asn Gln Phe Asn His
                20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
 65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
               100                 105                 110

Glu Gln Gly Asn Pro Asp Thr Leu Cys Met Asp Tyr Asn
           115                 120                 125

<210> SEQ ID NO 18
<211> LENGTH: 125
<212> TYPE: PRT
<213> ORGANISM: Homo sapiens

<400> SEQUENCE: 18

Ala Ser Lys Ala Pro Val Cys Gln Glu Ile Thr Val Pro Met Cys Arg
 1               5                  10                  15

Gly Ile Gly Tyr Asn Leu Thr His Met Pro Asn Gln Phe Asn His Asp
                20                  25                  30

Thr Gln Asp Glu Ala Gly Leu Glu Val His Gln Phe Trp Pro Leu Val
            35                  40                  45

Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
 65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
               100                 105                 110

Leu Gly Arg Asp Ala Glu Val Leu Cys Met Asp Tyr Asn
           115                 120                 125

<210> SEQ ID NO 19
<211> LENGTH: 162
<212> TYPE: PRT
<213> ORGANISM: Homo sapiens

<400> SEQUENCE: 19

Val Arg Ala Gln Ala Ala Gly Gln Gly Pro Gly Gln Gly Pro Gly Pro
 1               5                  10                  15

Gly Gln Gln Pro Pro Pro Pro Gln Gln Gln Ser Gly Gln Gln
                20                  25                  30
```

```
Tyr Asn Gly Glu Arg Gly Ile Ser Val Pro Asp His Gly Tyr Cys Gln
            35                  40                  45

Pro Ile Ser Ile Pro Leu Cys Thr Asp Ile Ala Tyr Asn Gln Thr Ile
 50                  55                  60

Met Pro Asn Leu Leu Gly His Thr Asn Gln Glu Asp Ala Gly Leu Glu
 65                  70                  75                  80

Val His Gln Phe Tyr Pro Leu Val Lys Val Gln Cys Ser Ala Glu Leu
                85                  90                  95

Lys Phe Phe Leu Cys Ser Met Tyr Ala Pro Val Cys Thr Val Leu Glu
            100                 105                 110

Gln Ala Leu Pro Pro Cys Arg Ser Leu Cys Glu Arg Ala Arg Gln Gly
            115                 120                 125

Cys Glu Ala Leu Met Asn Lys Phe Gly Phe Gln Trp Pro Asp Thr Leu
130                 135                 140

Lys Cys Glu Lys Phe Pro Val His Gly Ala Gly Glu Leu Cys Val Gly
145                 150                 155                 160

Gln Asn

<210> SEQ ID NO 20
<211> LENGTH: 131
<212> TYPE: PRT
<213> ORGANISM: Homo sapiens

<400> SEQUENCE: 20

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45

Glu Val His Gln Phe Tyr Pro Leu Val Lys Val Gln Cys Ser Pro Glu
 50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
            115                 120                 125

Gly Gln Asn
130

<210> SEQ ID NO 21
<211> LENGTH: 132
<212> TYPE: PRT
<213> ORGANISM: Homo sapiens

<400> SEQUENCE: 21

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
                20                  25                  30

Thr Ile Leu Pro Asn Leu Leu Gly His Thr Asn Gln Glu Asp Ala Gly
            35                  40                  45

Leu Glu Val His Gln Phe Tyr Pro Leu Val Lys Val Gln Cys Ser Pro
```

```
            50                  55                  60
Glu Leu Arg Phe Phe Leu Cys Ser Met Tyr Ala Pro Val Cys Thr Val
 65                  70                  75                  80

Leu Asp Gln Ala Ile Pro Pro Cys Arg Ser Leu Cys Glu Arg Ala Arg
                 85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
            115                 120                 125

Val Gly Gln Asn
        130

<210> SEQ ID NO 22
<211> LENGTH: 134
<212> TYPE: PRT
<213> ORGANISM: Homo sapiens

<400> SEQUENCE: 22

Leu Glu Ile Gly Arg Phe Asp Pro Glu Arg Gly Arg Gly Ala Ala Pro
 1               5                  10                  15

Cys Gln Ala Val Glu Ile Pro Met Cys Arg Gly Ile Gly Tyr Asn Leu
                20                  25                  30

Thr Arg Met Pro Asn Leu Leu Gly His Thr Ser Gln Gly Glu Ala Ala
            35                  40                  45

Ala Glu Leu Ala Glu Phe Ala Pro Leu Val Gln Tyr Gly Cys His Ser
 50                  55                  60

His Leu Arg Phe Phe Leu Cys Ser Leu Tyr Ala Pro Met Cys Thr Asp
 65                  70                  75                  80

Gln Val Ser Thr Pro Ile Pro Ala Cys Arg Pro Met Cys Glu Gln Ala
                85                  90                  95

Arg Leu Arg Cys Ala Pro Ile Met Glu Gln Phe Asn Phe Gly Trp Pro
            100                 105                 110

Asp Ser Leu Asp Cys Ala Arg Leu Pro Thr Arg Asn Asp Pro His Ala
            115                 120                 125

Leu Cys Met Glu Ala Pro
        130

<210> SEQ ID NO 23
<211> LENGTH: 131
<212> TYPE: PRT
<213> ORGANISM: Homo sapiens

<400> SEQUENCE: 23

Ile Ser Ser Met Asp Met Glu Arg Pro Gly Asp Gly Lys Cys Gln Pro
 1               5                  10                  15

Ile Glu Ile Pro Met Cys Lys Asp Ile Gly Tyr Asn Met Thr Arg Met
                20                  25                  30

Pro Asn Leu Met Gly His Glu Asn Gln Arg Glu Ala Ala Ile Gln Leu
            35                  40                  45

His Glu Phe Ala Pro Leu Val Glu Tyr Gly Cys His Gly His Leu Arg
 50                  55                  60

Phe Phe Leu Cys Ser Leu Tyr Ala Pro Met Cys Thr Glu Gln Val Ser
 65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
```

Asp Cys Arg Lys Leu Pro Asn Lys Asn Asp Pro Asn Tyr Leu Cys Met
            115                 120                 125

Glu Ala Pro
        130

<210> SEQ ID NO 24
<211> LENGTH: 126
<212> TYPE: PRT
<213> ORGANISM: Homo sapiens

<400> SEQUENCE: 24

Phe Gly Asp Glu Glu Arg Arg Cys Asp Pro Ile Arg Ile Ser Met
1               5                   10                  15

Cys Gln Asn Leu Gly Tyr Asn Val Thr Lys Met Pro Asn Leu Val Gly
                20                  25                  30

His Glu Leu Gln Thr Asp Ala Glu Leu Gln Leu Thr Thr Phe Thr Pro
            35                  40                  45

Leu Ile Gln Tyr Gly Cys Ser Ser Gln Leu Gln Phe Phe Leu Cys Ser
        50                  55                  60

Val Tyr Val Pro Met Cys Thr Glu Lys Ile Asn Ile Pro Ile Gly Pro
65                  70                  75                  80

Cys Gly Gly Met Cys Leu Ser Val Lys Arg Arg Cys Glu Pro Val Leu
                85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro
        115                 120                 125

<210> SEQ ID NO 25
<211> LENGTH: 121
<212> TYPE: PRT
<213> ORGANISM: Homo sapiens

<400> SEQUENCE: 25

Arg Gly Ala Pro Cys Glu Ala Val Arg Ile Pro Met Cys Arg His Met
1               5                   10                  15

Pro Trp Asn Ile Thr Arg Met Pro Asn His Leu His His Ser Thr Gln
                20                  25                  30

Glu Asn Ala Ile Leu Ala Ile Glu Gln Tyr Glu Glu Leu Val Asp Val
            35                  40                  45

Asn Cys Ser Ala Val Leu Arg Phe Phe Leu Cys Ala Met Tyr Ala Pro
        50                  55                  60

Ile Cys Thr Leu Glu Phe Leu His Asp Pro Ile Lys Pro Cys Lys Ser
65                  70                  75                  80

Val Cys Gln Arg Ala Arg Asp Asp Cys Glu Pro Leu Met Lys Met Tyr
                85                  90                  95

Asn His Ser Trp Pro Glu Ser Leu Ala Cys Asp Glu Leu Pro Val Tyr
            100                 105                 110

Asp Arg Gly Val Cys Ile Ser Pro Glu
        115                 120

<210> SEQ ID NO 26
<211> LENGTH: 119
<212> TYPE: PRT
<213> ORGANISM: Homo sapiens

<400> SEQUENCE: 26

```
Ala Ala Cys Glu Pro Val Arg Ile Pro Leu Cys Lys Ser Leu Pro Trp
 1               5                  10                  15

Asn Met Thr Lys Met Pro Asn His Leu His Ser Thr Gln Ala Asn
             20                  25                  30

Ala Ile Leu Ala Ile Glu Gln Phe Glu Gly Leu Leu Gly Thr His Cys
         35                  40                  45

Ser Pro Asp Leu Leu Phe Phe Leu Cys Ala Met Tyr Ala Pro Ile Cys
 50                  55                  60

Thr Ile Asp Phe Gln His Glu Pro Ile Lys Pro Cys Lys Ser Val Cys
 65                  70                  75                  80

Glu Arg Ala Arg Gln Gly Cys Glu Pro Ile Leu Ile Lys Tyr Arg His
             85                  90                  95

Ser Trp Pro Glu Asn Leu Ala Cys Glu Glu Leu Pro Val Tyr Asp Arg
             100                 105                 110

Gly Val Cys Ile Ser Pro Glu
            115
```

```
<210> SEQ ID NO 27
<211> LENGTH: 122
<212> TYPE: PRT
<213> ORGANISM: Homo sapiens

<400> SEQUENCE: 27

His Ser Leu Phe Thr Cys Glu Pro Ile Thr Val Pro Arg Cys Met Lys
 1               5                  10                  15

Met Ala Tyr Asn Met Thr Phe Phe Pro Asn Leu Met Gly His Tyr Asp
             20                  25                  30

Gln Ser Ile Ala Ala Val Glu Met Glu His Phe Leu Pro Leu Ala Asn
         35                  40                  45

Leu Glu Cys Ser Pro Asn Ile Glu Thr Phe Leu Cys Lys Ala Phe Val
 50                  55                  60

Pro Thr Cys Ile Glu Gln Ile His Val Val Pro Pro Cys Arg Lys Leu
 65                  70                  75                  80

Cys Glu Lys Val Tyr Ser Asp Cys Lys Lys Leu Ile Asp Thr Phe Gly
             85                  90                  95

Ile Arg Trp Pro Glu Glu Leu Glu Cys Asp Arg Leu Gln Tyr Cys Asp
             100                 105                 110

Glu Thr Val Pro Val Thr Phe Asp Pro His
            115                 120
```

```
<210> SEQ ID NO 28
<211> LENGTH: 127
<212> TYPE: PRT
<213> ORGANISM: Homo sapiens

<400> SEQUENCE: 28

Gly His Ile Gly Gly His Ser Leu Phe Ser Cys Glu Pro Ile Thr Leu
 1               5                  10                  15

Arg Met Cys Gln Asp Leu Pro Tyr Asn Thr Thr Phe Met Pro Asn Leu
             20                  25                  30

Leu Asn His Tyr Asp Gln Gln Thr Ala Ala Leu Ala Met Glu Pro Phe
         35                  40                  45

His Pro Met Val Asn Leu Asp Cys Ser Arg Asp Phe Arg Pro Phe Leu
 50                  55                  60

Cys Ala Leu Tyr Ala Pro Ile Cys Met Glu Tyr Gly Arg Val Thr Leu
 65                  70                  75                  80
```

-continued

```
Pro Cys Arg Arg Leu Cys Gln Arg Ala Tyr Ser Glu Cys Ser Lys Leu
                85                  90                  95

Met Glu Met Phe Gly Val Pro Trp Pro Glu Asp Met Glu Cys Ser Arg
            100                 105                 110

Phe Pro Asp Cys Asp Glu Pro Tyr Pro Arg Leu Val Asp Leu Asn
        115                 120                 125

<210> SEQ ID NO 29
<211> LENGTH: 40
<212> TYPE: PRT
<213> ORGANISM: Homo sapiens

<400> SEQUENCE: 29

Cys Met Asn Leu Pro Tyr Asn Ser Thr Ser Tyr Pro Asn Tyr Phe Gly
1               5                   10                  15

His Arg Thr Gln Lys Glu Ala Ser Ile Ser Trp Glu Ser Ser Leu Phe
            20                  25                  30

Pro Ala Leu Val Gln Thr Asn Cys
        35                  40

<210> SEQ ID NO 30
<211> LENGTH: 40
<212> TYPE: PRT
<213> ORGANISM: Mus musculus

<400> SEQUENCE: 30

Cys Met Asn Leu Leu Tyr Asn His Thr His Tyr Pro Asn Tyr Leu Gly
1               5                   10                  15

His Arg Thr Gln Lys Glu Ala Ser Ile Ser Trp Glu Ser Ser Leu Phe
            20                  25                  30

Pro Ala Leu Val Gln Thr Asn Cys
        35                  40

<210> SEQ ID NO 31
<211> LENGTH: 40
<212> TYPE: PRT
<213> ORGANISM: Rattus norvegicus

<400> SEQUENCE: 31

Cys Met Asn Leu Pro Tyr Asn Leu Thr His Tyr Pro Asn Tyr Leu Gly
1               5                   10                  15

His Arg Thr Gln Lys Glu Ala Ser Ile Ser Trp Glu Ser Ala Leu Phe
            20                  25                  30

Pro Ala Leu Val Gln Thr Asn Cys
        35                  40

<210> SEQ ID NO 32
<211> LENGTH: 38
<212> TYPE: PRT
<213> ORGANISM: Homo sapiens

<400> SEQUENCE: 32

Cys Lys Gly Ile Gly Tyr Asn Tyr Thr Tyr Met Pro Asn Gln Phe Asn
1               5                   10                  15

His Asp Thr Gln Asp Glu Ala Gly Leu Glu Val His Gln Phe Trp Pro
            20                  25                  30

Leu Val Glu Ile Gln Cys
        35
```

```
<210> SEQ ID NO 33
<211> LENGTH: 38
<212> TYPE: PRT
<213> ORGANISM: Homo sapiens

<400> SEQUENCE: 33

Cys Arg Gly Ile Gly Tyr Asn Leu Thr His Met Pro Asn Gln Phe Asn
1               5                   10                  15

His Asp Thr Gln Asp Glu Ala Gly Leu Glu Val His Gln Phe Trp Pro
            20                  25                  30

Leu Val Glu Ile Gln Cys
        35

<210> SEQ ID NO 34
<211> LENGTH: 38
<212> TYPE: PRT
<213> ORGANISM: Homo sapiens

<400> SEQUENCE: 34

Cys Thr Asp Ile Ala Tyr Asn Gln Thr Ile Met Pro Asn Leu Leu Gly
1               5                   10                  15

His Thr Asn Gln Glu Asp Ala Gly Leu Glu Val His Gln Phe Tyr Pro
            20                  25                  30

Leu Val Lys Val Gln Cys
        35

<210> SEQ ID NO 35
<211> LENGTH: 38
<212> TYPE: PRT
<213> ORGANISM: Homo sapiens

<400> SEQUENCE: 35

Cys Thr Asp Ile Ala Tyr Asn Gln Thr Ile Met Pro Asn Leu Leu Gly
1               5                   10                  15

His Thr Asn Gln Glu Asp Ala Gly Leu Glu Val His Gln Phe Tyr Pro
            20                  25                  30

Leu Val Lys Val Gln Cys
        35

<210> SEQ ID NO 36
<211> LENGTH: 38
<212> TYPE: PRT
<213> ORGANISM: Homo sapiens

<400> SEQUENCE: 36

Cys Thr Asp Ile Ala Tyr Asn Gln Thr Ile Leu Pro Asn Leu Leu Gly
1               5                   10                  15

His Thr Asn Gln Glu Asp Ala Gly Leu Glu Val His Gln Phe Tyr Pro
            20                  25                  30

Leu Val Lys Val Gln Cys
        35

<210> SEQ ID NO 37
<211> LENGTH: 38
<212> TYPE: PRT
<213> ORGANISM: Homo sapiens

<400> SEQUENCE: 37

Cys Arg Gly Ile Gly Tyr Asn Leu Thr Arg Met Pro Asn Leu Leu Gly
1               5                   10                  15

His Thr Ser Gln Gly Glu Ala Ala Ala Glu Leu Ala Glu Phe Ala Pro
```

```
                20                  25                  30

Leu Val Gln Tyr Gly Cys
         35

<210> SEQ ID NO 38
<211> LENGTH: 38
<212> TYPE: PRT
<213> ORGANISM: Homo sapiens

<400> SEQUENCE: 38

Cys Lys Asp Ile Gly Tyr Asn Met Thr Arg Met Pro Asn Leu Met Gly
1               5                   10                  15

His Glu Asn Gln Arg Glu Ala Ala Ile Gln Leu His Glu Phe Ala Pro
                20                  25                  30

Leu Val Glu Tyr Gly Cys
         35

<210> SEQ ID NO 39
<211> LENGTH: 38
<212> TYPE: PRT
<213> ORGANISM: Homo sapiens

<400> SEQUENCE: 39

Cys Gln Asn Leu Gly Tyr Asn Val Thr Lys Met Pro Asn Leu Val Gly
1               5                   10                  15

His Glu Leu Gln Thr Asp Ala Glu Leu Gln Leu Thr Thr Phe Thr Pro
                20                  25                  30

Leu Ile Gln Tyr Gly Cys
         35

<210> SEQ ID NO 40
<211> LENGTH: 38
<212> TYPE: PRT
<213> ORGANISM: Homo sapiens

<400> SEQUENCE: 40

Cys Arg His Met Pro Trp Asn Ile Thr Arg Met Pro Asn His Leu His
1               5                   10                  15

His Ser Thr Gln Glu Asn Ala Ile Leu Ala Ile Glu Gln Tyr Glu Glu
                20                  25                  30

Leu Val Asp Val Asn Cys
         35

<210> SEQ ID NO 41
<211> LENGTH: 38
<212> TYPE: PRT
<213> ORGANISM: Homo sapiens

<400> SEQUENCE: 41

Cys Lys Ser Leu Pro Trp Asn Met Thr Lys Met Pro Asn His Leu His
1               5                   10                  15

His Ser Thr Gln Ala Asn Ala Ile Leu Ala Ile Glu Gln Phe Glu Gly
                20                  25                  30

Leu Leu Gly Thr His Cys
         35

<210> SEQ ID NO 42
<211> LENGTH: 38
<212> TYPE: PRT
<213> ORGANISM: Homo sapiens
```

-continued

```
<400> SEQUENCE: 42

Cys Met Lys Met Ala Tyr Asn Met Thr Phe Phe Pro Asn Leu Met Gly
1               5                   10                  15

His Tyr Asp Gln Ser Ile Ala Ala Val Glu Met Glu His Phe Leu Pro
            20                  25                  30

Leu Ala Asn Leu Glu Cys
        35

<210> SEQ ID NO 43
<211> LENGTH: 38
<212> TYPE: PRT
<213> ORGANISM: Homo sapiens

<400> SEQUENCE: 43

Cys Gln Asp Leu Pro Tyr Asn Thr Thr Phe Met Pro Asn Leu Leu Asn
1               5                   10                  15

His Tyr Asp Gln Gln Thr Ala Ala Leu Ala Met Glu Pro Phe His Pro
            20                  25                  30

Met Val Asn Leu Asp Cys
        35
```

ANTI TUMORAL IMMUNOGENIC PEPTIDES AND VACCINE THEREOF

CROSS REFERENCE TO RELATED APPLICATIONS

This application is a U.S. national phase of PCT/IT2005/000780 filed Dec. 29, 2005, the contents of which are hereby incorporated by reference. The PCT application published in English as WO2006/070432 A2.

SEQUENCE LISTING

The instant application contains a Sequence Listing which has been submitted in ASCII format via EFS-Web and is hereby incorporated by reference in its entirety. Said ASCII copy, created on Nov. 29, 2012, is named 02607300.txt and is 26,449 bytes in size.

The present invention refers to novel immunogenic peptide sequences in connection with tumors, particularly colon rectal carcinoma and uses thereof for the preparation of vaccines.

It is known that Corin protein is type II trans-membrane serine protease acting as natriuretic proatrial factor (proANP) convertase in the heart (Yan et al. 1999). Therefore Corin expression pattern is considered very similar to that of natriuretic peptides.

In addition to the heart the Corin expression (AF133845) has been detected in other tissues, like kidney during the development, bone and uterus. Even more surprisingly Corin expression has been detected also in various sarcomas and carcinomas, as lung carcinoma, small cell lung cancer (SCLC) (Wu et al, 2003), osteosarcomas, leiomyosarcomas, endometrial carcinomas, but expression analysis results in colon or colon carcinoma have not been disclosed yet (as from reference research in PubMed).

Corin protein is a protease which in addition to serine protease domain presents in the extra-cellular region two cysteine rich domains (Frizzled like) which are common to Wnt factor interacting but not trypsin-like protease proteins (serine protease). Corin amino acid sequences of rat, mouse and human together with other "Frizzled" proteins (Fz, soluble or trans-membrane receptor) are represented as in alignment in FIG. 1 to show the high retention degree of cysteine rich domains (CRD). These domains include about 120 amino acids with unaltered pattern of 10 cysteine residues (numbered in the lower of the figure) forming five bi-sulfide bridges resulting in alpha-helix structures. Region between $2^{nd}$ and 3rd cysteine residue is represented in more detail in FIG. 2. While correlation of inappropriate activation of Wnt/Fz factor transduction system with carcinogenesis is known (Holcombe et al., 2002; Vincan et al. 2003), it is not the same for the relation of the latter and serine-protease with Frizzled-like domains, for example Corin.

Up to now the need to provide novel vaccine against tumors suitable to generate an immune response suitable to contain tumor growth to be used in combination with chemotherapy or radiotherapy exists.

In this context WO 01/62786 discloses a TLP protein system peptide (SEQ ID No: 2) or fragments thereof to be used as antigens in anti-tumor vaccine, particularly lung tumor. Specifically WO 98/15282 discloses a few TLP peptides with SEQ ID No: 1 SEQ ID No: 2 or SEQ ID No: 3 sequences already described in WO-A-001458, to be used as immunogens for the preparation of anti-tumor vaccine, particularly for lung, urogenital tumors and not small cell lung carcinoma (NSCLC).

However above reported peptides suffer from the disadvantage to be poorly immunogenic as reported in WO 03/045997, wherein fusion proteins from these peptides and IL-2 and use thereof as anti-tumor antigens for the prevention and treatment of various tumors are disclosed.

Colon carcinoma is one of the most frequent pathologies in developed countries. In Europe both in male and female the colon rectal tumor is the second most diffused neoplasia (Ferlay et al., 1999). Incidence thereof is higher in European Caucasian than Asiatic and African populations. (Parkin et al. 2002).

The authors of present invention now have discovered some peptide sequences within one of Corin cysteine rich domains (NCBI NC_00004; gi: 37625049), able to act as immunogens to provide an anti-tumor vaccine specifically designed for Caucasian population (HLA A0210, HLA A03, HLA B0702, HLA B2705, HLA B5101 alleles).

T and B cells recognize protein antigens according to substantially different patterns. While B cell receptors and antibodies recognize antigen in solution and bind linear or assembled 15-22 amino acid epitopes, T cell receptors recognize the antigen after proteolyitic degradation resulting in 8-11 and 12-25 amino acid segmental epitopes respectively bound to class I and II molecules encoded by major histocompatibility complex (MHC). Different length of MHC presented peptides is a function of the species and particular MHC I-II allele of the subject. In humans, particularly, mean length of HLA type I protein epitopes is 9-10 amino acids. Therefore in order to be used as antigen effectively presented by different HLA of the Caucasian population the peptides according to the invention must be at least nonamers because as it is known human MHC pouch prefers 9-10 amino acid peptides while with 8 or 12 amino acid peptides the antigen presentation is less effective.

The authors by means of ELISPOT assays (see Example 1, FIG. 3) proved these peptides to be more immunogenic because they generate higher antigen-specific response in DHD-K12 colon tumor inoculated rat lymphocytes than peptide described in WO 98/15282 and WO-A-001458 having RTNKEASI SEQ ID No: 1, whose poor immunogenicity has been already reported in WO 03/045997. Further RTNKEASI epitope is not naturally occurring, not being detected within mammalian Corin sequence. Effect of the immune response mainly is to purify epitope-positive cells or suppress epitope expression and generate a differentiation of the involved cells. Because RTNKEASI epitope is not the naturally occurring sequence it was impossible to detect immunogenic epitopes not having anti-self or false positive in immune response via not naturally occurring epitopes recognition.

Therefore immunogenic peptides comprising QKEASI (SEQ ID No: 1) sequence belonging to the region from cysteine 2 to cysteine 3 of the mammalian Corin protein Frizzled2 domain represent an object of the present invention. Preferably above said peptides are from 8 to 12 amino acid long.

According to a preferred embodiment the peptides according to the invention comprise RTQKEASI (SEQ ID No: 2) epitope, localized between cysteine 2 and 3 residues of Corin Frizzled2 domain (Frizzled 2 domain, Corin positions 531-570).

According to a particularly preferred aspect of the present invention (adaptability to human MHC pouch to result in an effective antigen presentation) peptides can be nonamers or decamers. Preferably peptides according to the invention comprise the HRTQKEASI (SEQ ID No: 3) (Corin positions 548-555) or RTQKEASIC (SEQ ID No: 4) sequence.

According to a further embodiment peptides of the invention as above defined can be such that amino acid residue R is replaced with M or P and/or the amino acid residue T is replaced with E, in order to optimize further the interaction of the peptide with various HLA-1 haplotypes.

According to a further aspect of the present invention the peptides can be characterized in that they have an end C-terminus cysteine residue.

More particularly the peptides according to the invention can be selected from the group consisting of: HRTQKEASI (SEQ ID No:3), HMTQKEASI (SEQ ID No:5), HREQKEASI (SEQ ID No:6), REQKEASI (SEQ ID No:7), MTQKEASI (SEQ ID No:8), RTQKEASI (SEQ ID No:2), HRTQKEASIC (SEQ ID No:9), RTQKEASIC (SEQ ID No:4), MTQKEASIC (SEQ ID No:10), REQKEASIC (SEQ ID No:11), HMTQKEASIC (SEQ ID No:12), HREQKEASIC (SEQ ID No:13).

Peptides as above alternatively can be protected at N-terminus or C-terminus to avoid the digestion before the immune stimulation occurs. Or sequence amino acids can be replaced with less hydrolysis susceptible residues.

DNA sequences encoding for as above defined peptides represent a further object of the invention, also considering the adaptation of the usage codon in various species (prokaryotic cells, insect cells, etc.).

A further object of the present invention is represented by an expression vector comprising at least an as above defined DNA sequence. According to a preferred embodiment the expression vector can further comprise the sequence encoding for an immunomodulating compound selected from the group consisting of immunomodulating chemokines and cytokines, like for example IL-12, IL-2, GM-CSF, INF-gamma o fusion proteins with vaccination adjuvant (tetanic toxin fragment C).

It is an object of the present invention the use of the above defined peptides or expression vector for the preparation of a vaccine for the preventive treatment of tumors, preferably colon rectal carcinoma in subjects of Caucasian population (HLA A0201, HLA A03, HLAB0702, HLA B2705, HLA B5101 alleles). Particularly the peptides according to the invention can be used in association with at least a chemotherapeutic agent (for example cyclophosphamide) and/or antibodies according to the invention.

Peptides according to the invention can be administered via any route suitable to stimulate an immune response and as single or multiple doses. In addition the peptides can be in vivo expressed by transformation with a viral, bacterial vector, plasmid, and the expression product can be also a fusion protein. Finally the peptides can be delivered using carrier molecules, as long as the epitope is effectively or in vivo exposed in order to allow the generation of immune response.

It is a further object of the present invention an anti-tumoral vaccine, preferably anti-colon rectal carcinoma, comprising at least one of the peptides or the expression vector as above defined together with pharmacologically acceptable adjuvants and excipients.

The present invention further relates to monoclonal or oligoclonal antibodies specific for one of the inventive peptides. Monoclonal antibodies according to the invention can be used also for the preparation of a medicament for the treatment of the tumors, preferably colon rectal carcinoma, to be administered directly into cancerous lesion and they can be used in association with chemotherapeutics.

It is a further object of the present invention a method for the in vitro determination of the tumor occurrence or follow-up of the patient suffering from the tumor, preferably colon rectal carcinoma, in a biological sample comprising the use of the monoclonal or polyclonal antibodies as above defined.

Finally an object of the present invention is a diagnostic kit comprising the monoclonal or oligoclonal antibodies as above defined for the determination of the tumor occurrence or follow-up of the patient suffering from the tumor, preferably colon rectal carcinoma.

The present invention now will be described by way of illustration but not limitation according to preferred embodiments thereof with particular reference to the enclosed drawings, wherein.

Figure 4:
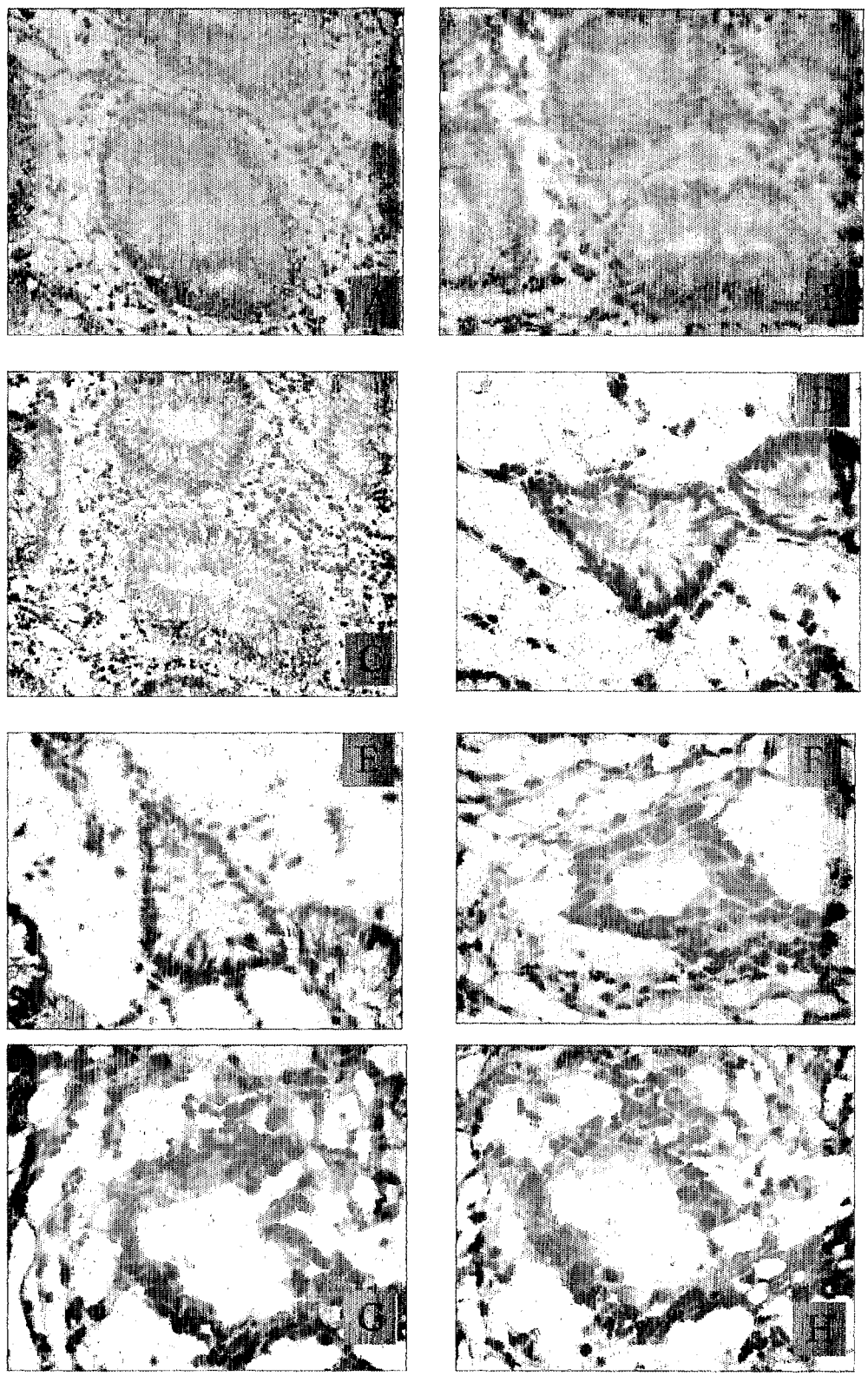
Figure 5:
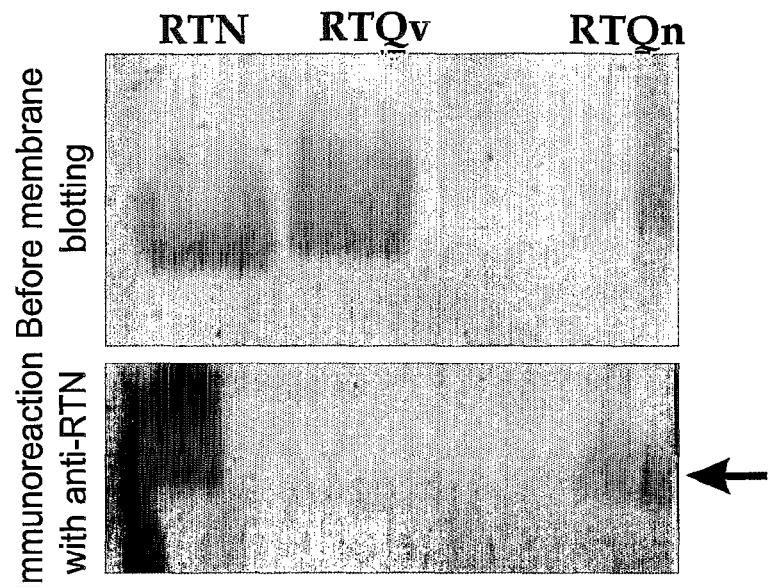
Figure 6:
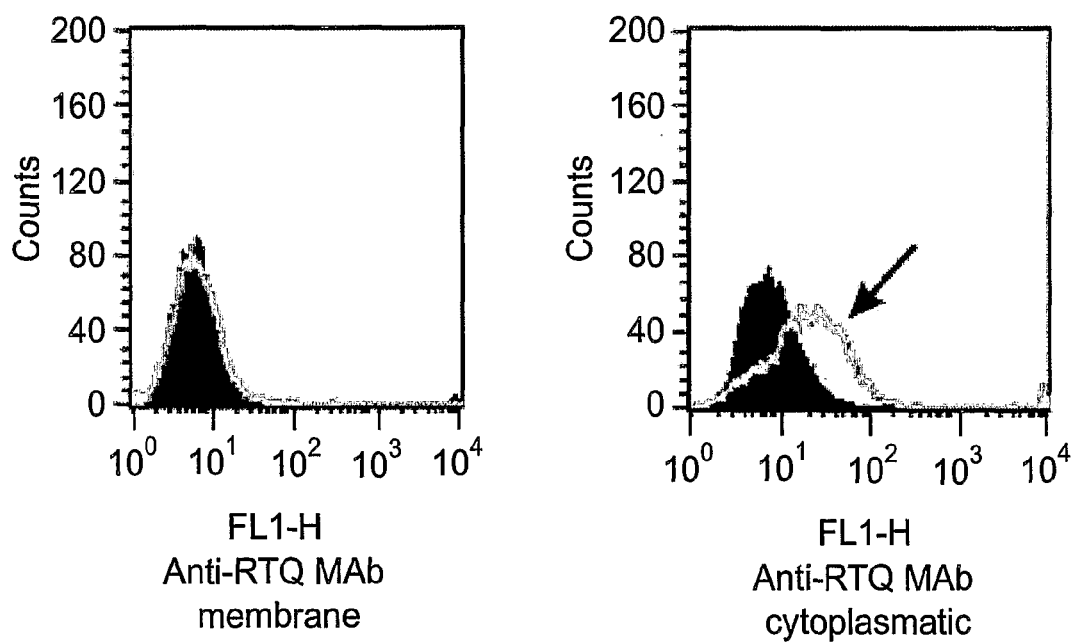
Figure 7:
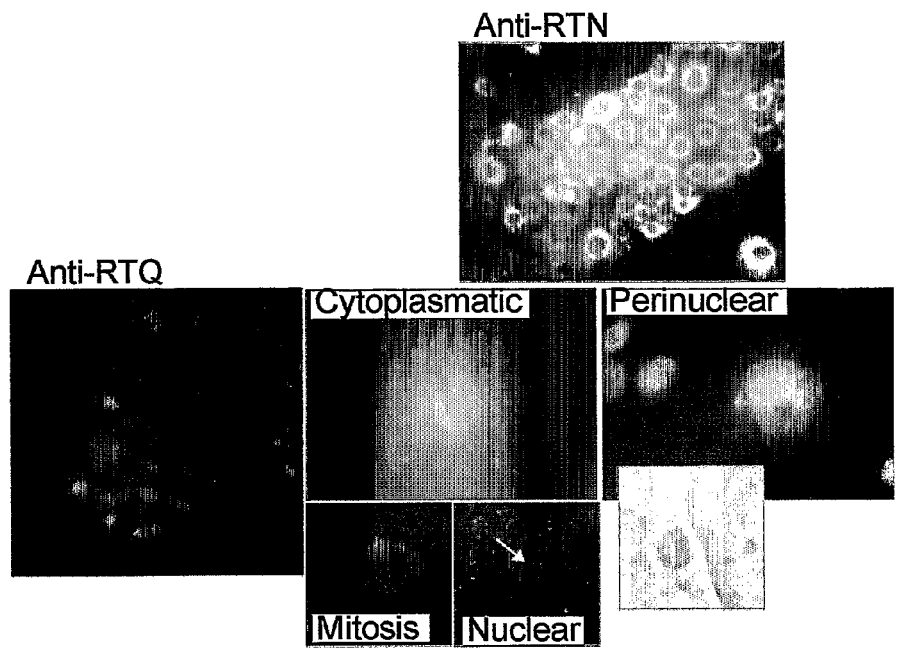
Figure 8:
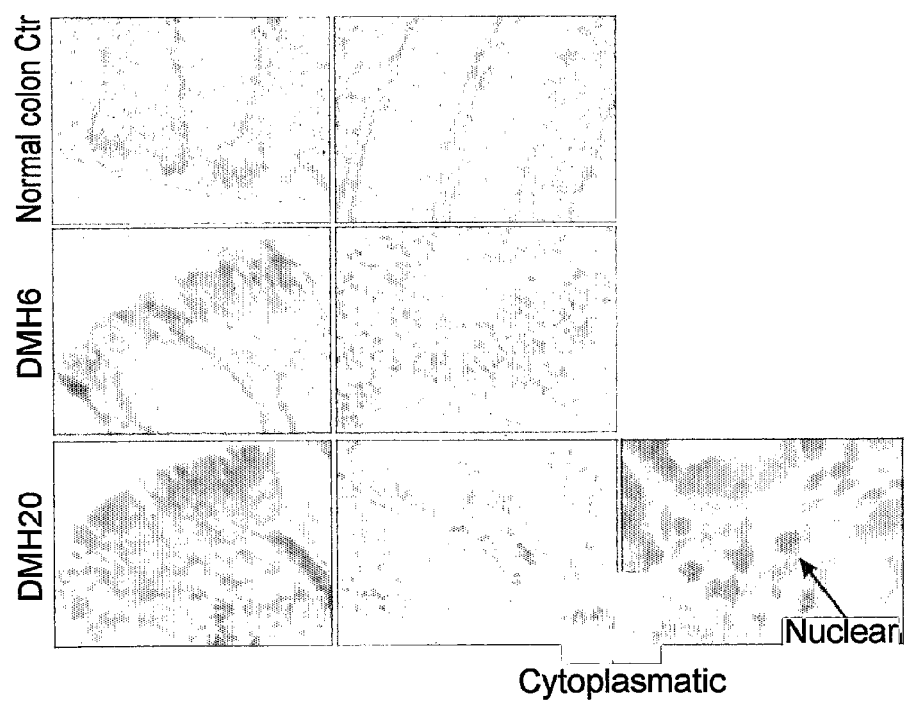
Figure 9:
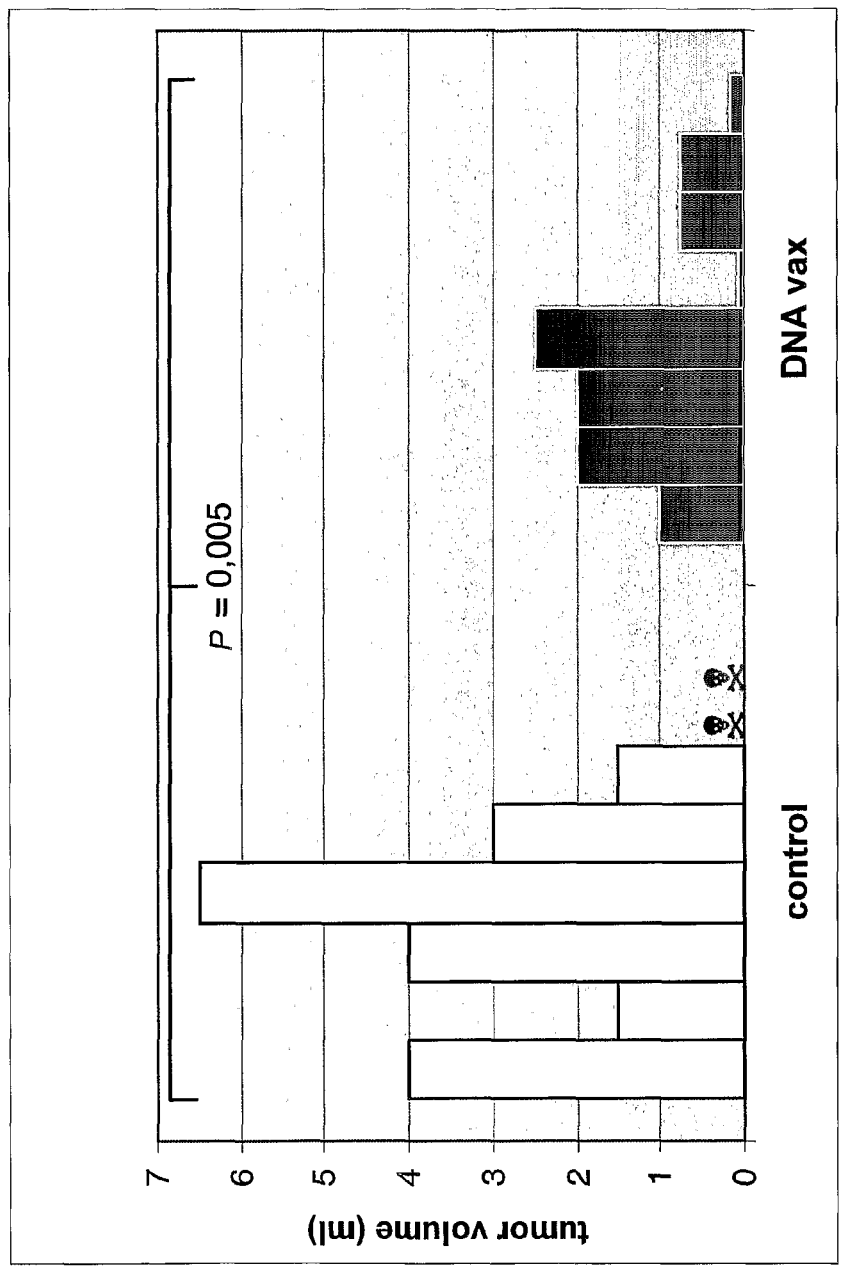

FIG. 4 in A-H panels shows immunohistochemical analyses of various control samples, normal colon mucosa, colon adenocarcinoma;

FIG. 5 shows immunoblot of anti-RTNKEASI polygonal antibody and reaction thereof with both RTNKEASI (lane 1) and RTQKEASI (SEQ ID NO:2) (lane arrow 3);

FIG. 6 shows cytofluorimetric analysis of DHD-K12 cells using membrane (left panel) and cytoplasmic (right panel) anti-RTQ monoclonal antibodies;

FIG. 7 shows immunofluorescence analysis of DHD-K12 cells using anti-RTQ monoclonal antibody to determine the intracellular distribution (vesicular, cytoplasmic, perinuclear, nuclear);

FIG. 8 shows immunohistochemical analysis using nuclear and cytoplasmic anti-RTQ monoclonal antibody of normal and DMH treated BDIX rat tissue colons; DMH6: sampling at $11^{th}$ week after DMH last dose; DMH20: sampling at $26^{th}$ week after DMH last dose;

FIG. 9 shows the effect of therapeutic immunization with RTQKEASI (SEQ ID NO:2) containing a DNA (DNA vax) vaccine on the reduction of the tumor volume in BDIX consanguineous rats after 9 growth weeks of colon carcinoma DHD-K12 syngenic cells (DHD-K12/BDIX) in comparison with a control (Freund's adjuvant),

EXAMPLE 1

Identification and Optimisation of the Most Frequent HLA-I Caucasian Alleles of the Corin Frizzled 2 Region Epitopes By the use of the program and data bank SYFPEITHI the amino acid sequence of Frizzled 2 region from cysteine 2 to cysteine 3 of the human and mouse Corin protein was determined in order to detect within this protein sequence various MHC-1 presentation candidate epitopes.

Computer analysis using SYFPEITHI program of the human and mouse (MHC-I: $H2-K^k$) amino acid sequences evidenced particularly two epitopes HRTQKEASI (SEQ ID NO:3) and RTQKEASI (SEQ ID NO:2), respectively.

The selection resulted mainly from two considerations:
both epitopes present an affinity score within "Medium" defined range, i.e. 10<x>20, 12 for HRTQKEASI (SEQ ID NO:3) human and 10 for RTQKEASI (SEQ ID NO:2) mouse epitopes, respectively;
further, as for HRTQKEASI (SEQ ID NO:3) human epitope, the same represents a good antigenic candidate for all HLA I alleles most frequent in Caucasian population (about 90% of population): HLA-A0201, -B2705, -B0702, -A03, -B510. In fact it is selected by SYFPEITHI program as candidate for MHC I optimisation in all these alleles according to the following score values for any considered allele:

HLA-A0201=Score 12
HLA-A03=Score 10
HLA-B2705=Score 20
HLA-B0702=Score 7
HLA-B5101=Score 11

As for score results from epitope prediction it has been further evaluated the role of HRTQKEASI (SEQ ID NO:3) amino acid sequence contained in human Corin Frizzled 2 (FRI.2) protein with respect to more frequent allele variants in the Caucasian population (HLA-A0201, -B27, -B0702, -A03 e -B5101).

From epitope prediction analysis carried out for MHC I allele more frequent in the Caucasian population, i.e. HLA-0201, considering FRI.2 amino acid sequence from 454 to 575 position, Score 12 nonarner epitope HRTOKEASI SEQ ID NO:3), containing the amino acid sequence from 479 to 487 position, has been selected. This epitope constitutes the best candidate for various above cited HLA-I alleles.

| HRTQKEASI epitope optimisation | | | | | | | | | |
|---|---|---|---|---|---|---|---|---|---|
| Position | | | | | | | | | |
| 1 | 2 | 3 | 4 | 5 | 6 | 7 | 8 | 9 | Score |
| HLA-A0201 (allele representing about 75% Caucasian population) | | | | | | | | | |
| H | R<br>↓<br>M | T | Q | K | E | A | S | I | 12<br>↓<br>22 |
| HLA-B27: | | | | | | | | | |
| H | R | T | Q | K<br>HLA-B0702: | E | A | S | I | 20 |
| H | R<br>↓<br>P | T | Q | K | E | A | S | I | 7<br>↓<br>17 |
| HLA-B5101: | | | | | | | | | |
| H | R<br>↓<br>P | T | Q | K | E | A | S | I | 11<br>↓<br>21 |

The $2^{nd}$ and $9^{th}$ are critical amino acids of optimal epitopes for HLA I alleles more frequent in the Caucasian population (-A0201, -B27, -B0702, -A03 and -B5101). According to above, the optimisation of the amino acids in these epitope positions with respect to specific pouches of any HLA-I allele allows the association score to be increased resulting in higher antigen presentation efficiency.

As result from this consideration RTNKEASI (SEQ ID No:1; WO-A-001458) octamer, selected as comparison term being most recent known art, cannot be efficiently presented because it has only 8 amino acids. If RTNKEASI epitope prediction for more frequent HLA-I alleles is estimated the result is null, i.e. it isn't presented efficiently.

EXAMPLE 2

Anti-Corin Antibodies Development and Immunohistochemistry

Based on above considerations RTQKEASI (SEQ ID NO:2) peptide was used to immunize mouse (CD2F1 strain) for the production of serum to be initially used for immunohistochemical experiments to verify the antigen expression in tissues.

Peptide was synthesized by INBIOS S.r.l. with >70% purity by HPLC, water solubility of 5 mg (0.1% TFA).

Immunization pattern was as below:
4 CD2F1 mouse were immunized subcutaneously with 100 mg/ml of ovalbumin adjuvant conjugated peptide;
$1^{st}$ immunization carried out with Freund's complete adjuvant;
from $2^{nd}$ immunization on Freund's not complete adjuvant was used for 5 immunizations in all.
sampling at $5^{th}$ day after last immunization In order to verify the presence of anti-RTQKEASI (SEAQ ID NO:2) specific antibodies an ELISA assay with well adsorbed peptide (10 mg/ml) was provided.

ELISA results are shown in Table 3 and expressed as OD values

TABLE 3

| | Dilution | OD(nm) |
|---|---|---|
| Negative control | | 0.141 |
| Animal 1 | 1:1000 | 0.251 |
| | 1:2500 | 0.216 |
| Animal 2 | 1:1000 | 0.210 |
| | 1:2500 | 0.177 |
| Animal 3 | 1:1000 | 0.156 |
| | 1:2500 | 0.121 |
| Animal 4 | 1:1000 | 0.276 |
| | 1:2500 | 0.190 |

Based on these results 3 out of 4 animals developed antibodies against RTQKEASI (SEQ ID NO:2).

Considering that smallest epitope which can be presented by the mice is 8 amino acid long, generated antibodies can be hypothetically considered analogous to monoclonal antibodies.

Antigenic Expression and Immunohistochemistry

Preliminary data available in the following sites:
OMIM
GEO Profiles
SAGE
SOURCE
GeneNote
GeneCard
for Corin (AF133845) up-to-date at time of filing demonstrate high expression levels of the protein in the heart (cardiomyocytes), kidney during the development and bone. Corin expression pattern is considered very similar to that of natriuretic peptides. The expression is demonstrated in not univocal mode also in other tissues (thymus, lung, prostate, etc.) and in osteosarcomas, leiomyosarcomas, endometrial carcinomas, but expression analysis results in colon or colon carcinoma have not been disclosed yet (analysis extended also to research at same date in PubMed "corin and colon".

Corin expression was evaluated by immunohistochemical assays in colon and colon carcinoma.

Analyzed tissues were respectively human colon adenocarcinomas and corresponding normal colon mucosa fragments.

Samples of adenocarcinoma and healthy neoplasia far-away tissue were newly collected previously and frozen directly at −80° C.

Lesions were characterized, staged and graded according to pathological anatomy standard and results are shown in Table 1.

TABLE 1

| Patient | Grade | TNM | Histotype | Corresponding normal tissue |
|---|---|---|---|---|
| A: | G3 | T3, N0, Mx | Classic histotype | Normal colon mucosa |
| B: | G3 | T3, N0, Mx | Classic histotype | Normal colon mucosa |
| C: | G3 | T4, N1, Mx | Classic histotype | Normal colon mucosa |
| D: | G2 | T3, N0, M1 | Histotype mucus secreting aspects | Normal colon mucosa |
| E: | G2 | T3, N0, Mx | Histotype mucus secreting aspects | Normal colon mucosa |

Immunohistochemical analysis was carried out using cryostat section preparations. Histological sections were then acetone fixed.

Histological sections were treated with mouse anti-RTKQEASI (SEQ ID NO:2) immune or pre-immune sera at 1/100 dilution. Reaction was detected using avidin-biotin and diaminobenzidine system.

Following controls were used:
negative controls without antibody to detect eventual cross-reactivity or aspecific diaminobenzidine precipitations;
negative control preimmune serum:
immune serum Results are reported in Table 2; cytoplasmic localization for the immunohistochemical results is most reasonable, yet it is not possible to exclude localization on cytoplasmic membrane.

TABLE 2

| Patient | | Positivity | Localization | G-TNM |
|---|---|---|---|---|
| A | Adenocarcinotna | +++ | cytoplasma | G3, T3, N0, Mx |
|   | Normal mucosa | +/− | cytoplasma |  |
| B | Adenocarcinoma | +++ | cytoplasma | G3, T3, N0, Mx |
|   | Normal mucosa | − |  |  |
| C | Adenocarcinoma | ++ | cytoplasma | G3, T4, N1, Mx |
|   | Normal mucosa | − |  |  |
| D | Adenocarcinoma | − |  | G2, T3, N0, M1 mucus secreting |
|   | Normal mucosa | − |  |  |
| E | Adenocarcinoma | ++ | cytoplasma | G2, T3, N0, Mx mucus secreting |
|   | Normal mucosa | − |  |  |

More specifically in FIG. 4, A and B panels, negative controls of immunohistochemical procedure without antibody and use of preimmune serum (1/100) for controlling immunohistochemical procedure and preimmune serum are shown, respectively. In the panel C of FIG. 4 immunohistochemical experiment with use of immune serum (17100) is shown. With respect to preimmune serum control (panel B) the cytoplasmic positivity of epithelial neoplastic cells is apparent.

FIG. 4, panel D, shows immunohistochemical analysis of negative control carried out on a normal colon mucosa sample using preimmune serum (1/100); panel E depicts immunohistochemical experiment carried out using immune serum (1/100). No significant staining variations are observed in comparison to preimmune serum control. FIG. 4, panel E, shows negative control without antibody and allows the control of immunohistochemical procedure; panel F shows immunohistochemical analysis of negative control using pre-immune serum (1/100) and allows the control of immune serum; panel H shows immunohistochemical experiment using immune serum (1/100). With respect to preimmune serum the cytoplasmic positivity of epithelial neoplastic cells is apparent.

Based on immunohistochemical data a specific Corin expression in colon carcinoma in comparison to non significantly detectable expression in corresponding normal colon mucosa (same patients) is evident.

This result is significantly remarkable in order to develop diagnostic or therapeutic methods using this protein or developed antibodies as carriers or therapeutic agents for colon carcinoma.

EXAMPLE 3

Study about RTQKEASIC Immunogenicity by ELISPOT Assay

Following synthetic peptides with nonamer sequences to be compared were acquired: RTQKEASIC (SEQ ID NO:4) (novel peptide) and RTNKEASIC (known art peptide).

RTQKEASIC (SEQ ID NO:41) expression was characterized with experimental rat animal model.

Autologous colon carcinoma DHD-K12 line cells were inoculated intra-splenically in BDIX rats. These cells metastatize at polmonar and hepatic level and naturally express the epitope common also to human colon rectal carcinoma (RTQKEASIC (SEQ ID NO:4)). To evaluate the relevance of RTQKEASIC (SEQ ID NO:4) antigen in antigen specific cytotoxic response BDIX rats were immunized with DHD-K12.

PBMC cytotoxic activity (cytotoxicity test based on the release of $^{51}$Cr or LDH) of BDIX rats against DHD-K12 cells was evaluated after immunization and tumor inoculum. BDIX rats do not show spontaneous cytotoxic activity against DHD-K12 cells while this is induced 15-30 days after the inoculum. Nonamer RTQKEASIC immunization induces high cytotoxic activity against DHD-K12. In addition this activity is significantly increased after tumor inoculum in pre-immunized in comparison to non immunized rats.

In the present study the ability of DHD-K12 immunized BDIX rat lymphocytes to recognize directly in vitro the specific antigen by means of synthetic peptide has been evaluated.

Rat lymphocytes were provided by intra-cardiac blood sampling in rats from different groups (control and immunized). Sampling was carried out at 12-20 days after tumor inoculum. Peripheral blood mononucleate cells (PBMC) were obtained by Ficoll gradient separation. Lymphocytes were used fresh or frozen.

ELISPOT assay that allows antigen specific response expressed in immunized rat lymphocytes in individual cell by detection of INF-γ production to be evaluated was used.

ELISPOT is a simple and very sensitive method for analysis in an individual cell of the cellular activation: it is used particularly for the analysis of immune specific responses generated by whole antigens or single peptides. Furthermore, based on analyzed cytokines it allows responses obtained from different cellular sub-populations to be detected and differentiated.

High affinity cytokine (presently INF-γ) specific monoclonal antibody is coated on a PVDF 96-well plate. Effector cells (200-250×10$^3$) are added and incubated for 24-48 hours in the presence of antigens (4-10 µg peptides).

In this period antigen specific cells will respond releasing INF-γ. During this incubation, because the antibody is immobilized next to the cells, secreted cytokine will be immobilized on the plate. After washing to remove cells and useless material a biotinylated antibody directed against a second cytokine epitope is added.

Enzyme (for example horseradish peroxidase (HRP)) conjugated streptavidin was then added. After appropriate incubations and washings a substrate suitable to develop stained spots in respondent cell response sites is added. The latter will be examined and counted by means of image analyzer (AELVIS). By comparing spot and seeded cell numbers the frequency of antigen recognizing cells will be achieved.

Figure 1:
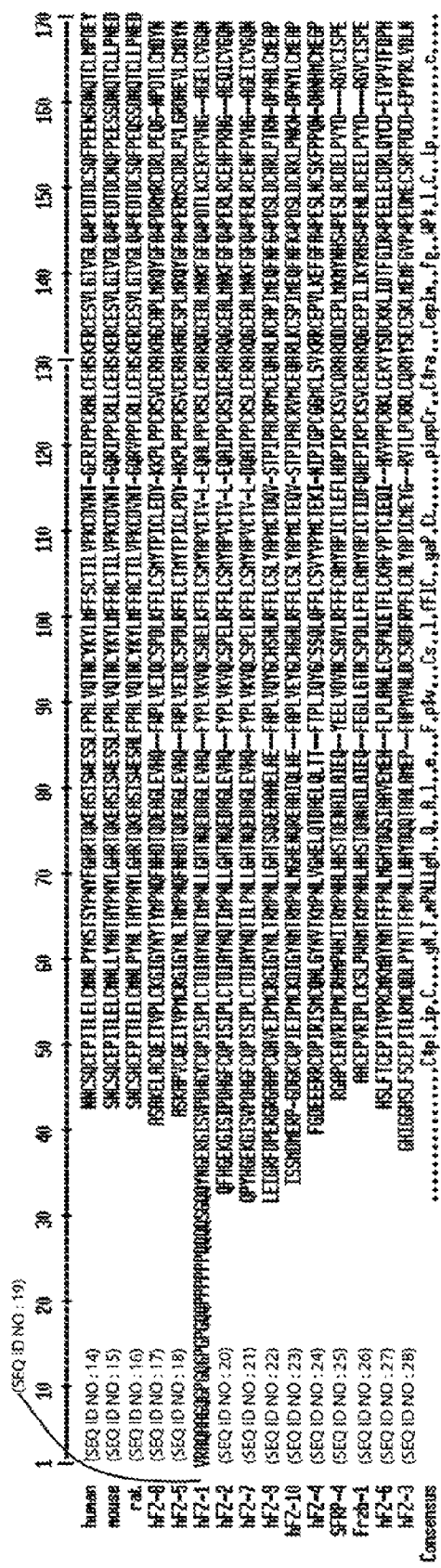
FIG. 1 shows the alignment of human, mouse and rat Corin Frizzled2 domain with respect to other membrane or secreted Frizzled sequences; ten cysteine residues are indicated with numerals in the lower.
Figure 2:
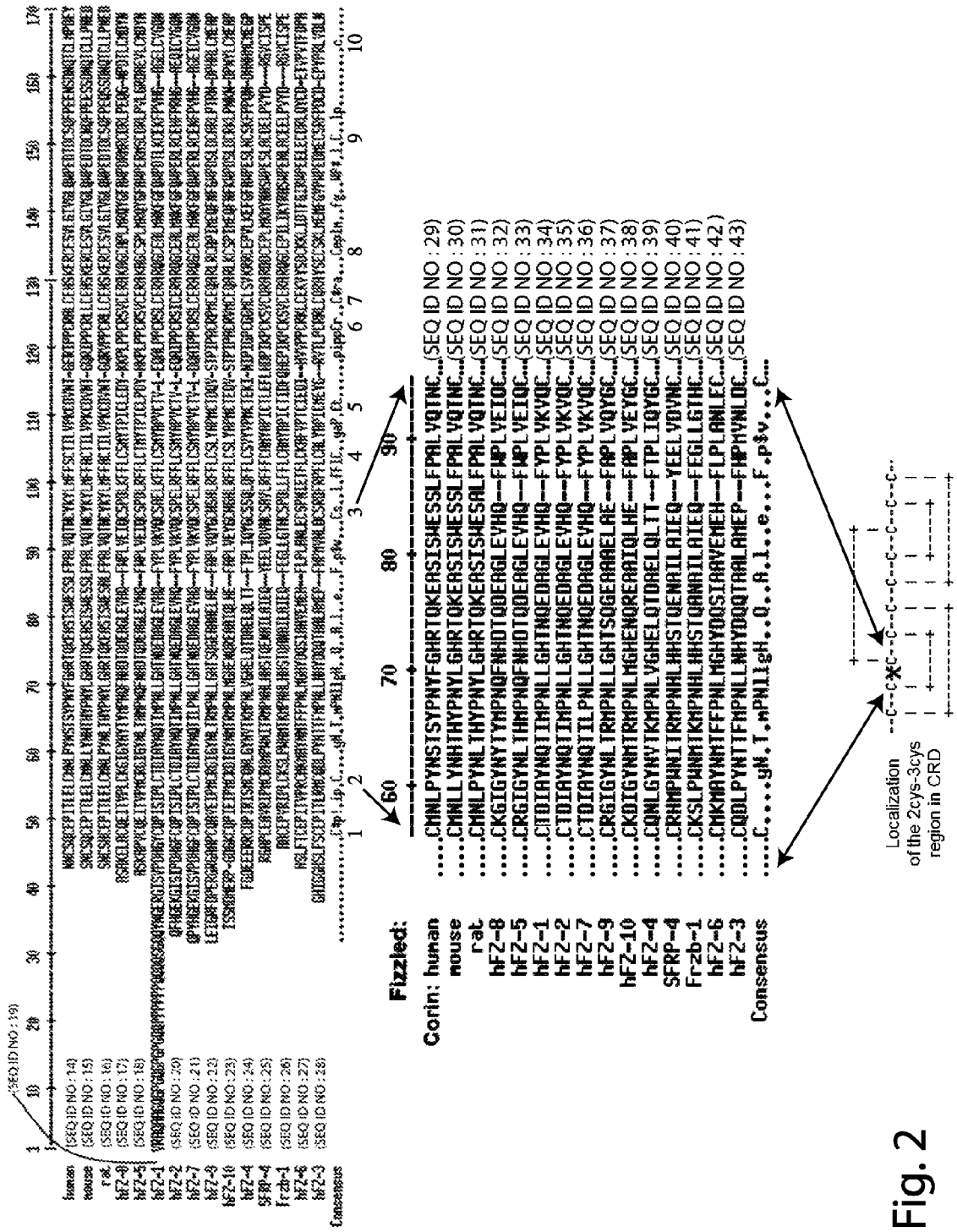
FIG. 2 shows with more detail the amino acid region from 2 to 3 Corin cysteine residues (Frizzled2)
Figure 3:
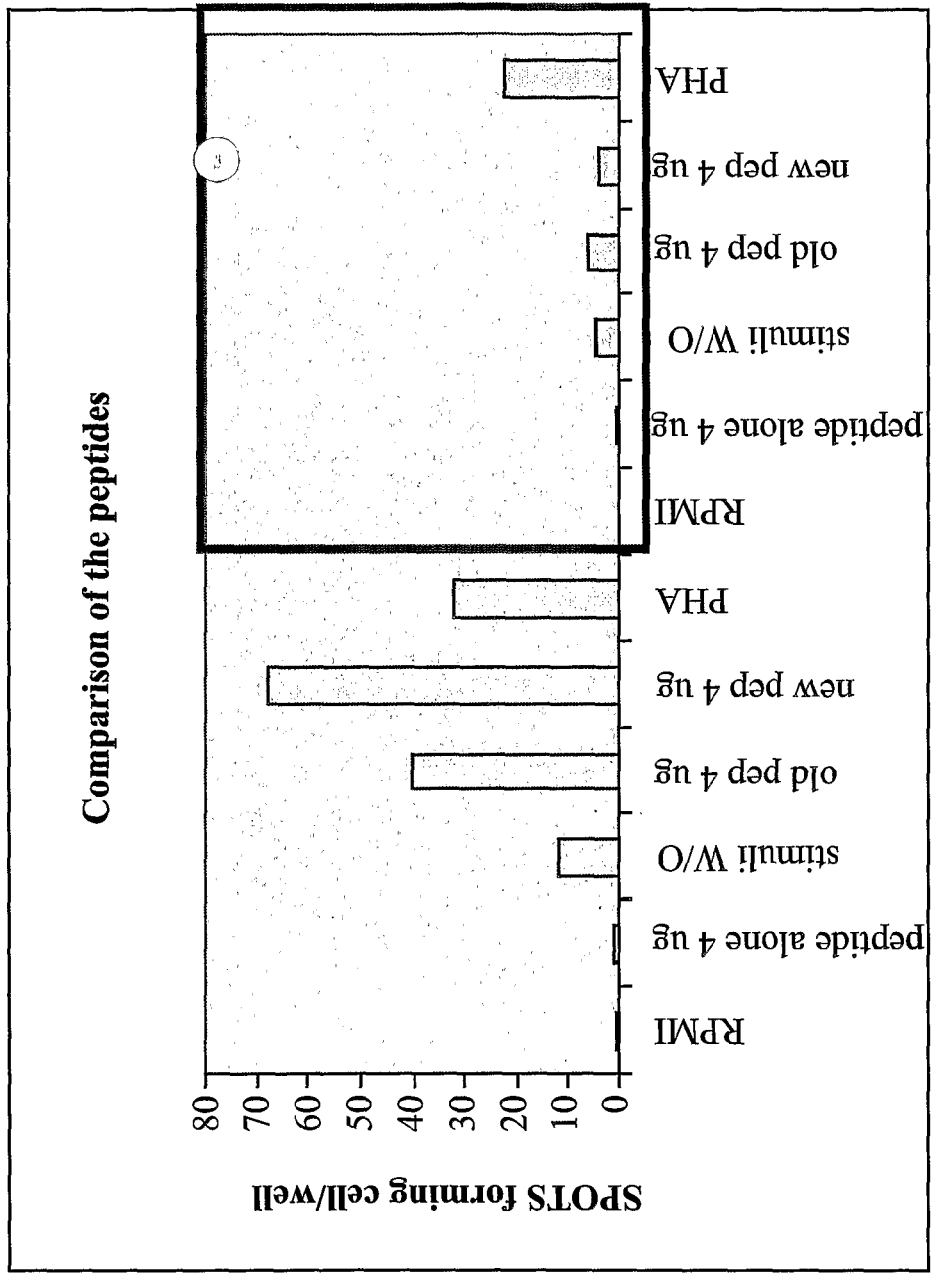
FIG. 3 shows ELISPOT comparative assay of nonamer peptides of the present invention and known art peptide.

In all the experiments samples to be assayed were used in triplicate or quadruplicate and results are expressed as mean of analyzed wells (FIG. 3). FIG. 3 shows comparison diagram of ELISPOT tests carried out by stimulation of $10 \times 10^6$ DHD cell i.p. inoculated rat lymphocytes with the two peptides. ELISPOT protocol in the present case includes $2 \times 10^6$ cell/ml and 200000 cell/well. Within the box results from control rats are shown. From the histogram analysis it results that in fact RTQKEASIC (SEQ ID NO:4) nonamer is more immunogenic than RTNKEASIC nonamer.

EXAMPLE 4

Study about Anti-RTQKEASI Vs Anti-RTNKEASI Antibody Specificity

Materials and Methods
Western Blot

In order to verify the reaction of anti-RTN polyclonal antibody (directed against RTNKEASI peptide sequence) against RTQKEASI (SEQ ID NO:2). peptide sequence by immunoblotting, 5 µg of anyone peptide were loaded on 18% SDS-gel polyacrylamide and transferred on PVDF membrane. Then the membrane was saturated with 5% PBS powder milk containing 0.05% Tween (PBST), incubated with 1:100 diluted anti-RTN in saturation buffer to identify the peptides and the reaction was detected with peroxidase conjugated secondary antibodies. After washing with PBST blot was developed using Super Signal System (Pierce). For the study of the antigen expression in DHD/K12 cells using both anti-RTN polyclonal and anti-RTQ monoclonal antibodies, cells were lysed in phosphate buffer, pH 6.8, containing 1% Triton-X 100, 100 IU/ml aprotinin and 1 mM PMSF. Solubilized proteins (42 µg) were loaded on 8% SDS-gel polyacrylamide and transferred on PVDF membrane. Antigen was identified with specific antibodies (1:100 diluted anti-RTN, 1:20 diluted anti-RTQ) and detected with peroxidase conjugated secondary antibodies.
Fluorescence Microscopy and Immunohistochemistry Confocal microscope detection of the antigen expression in DHD/K12 cells was carried out on 4% paraformaldehyde fixed, Triton-X 100 permeabilized and both anti-RTN (1:70 diluted) polyclonal and anti-RTQ (1.20 diluted) monoclonal antibody immunolabeled samples. The reaction was detected using Alexa 488 conjugated secondary antibodies. Cell nucleuses were contra-stained with propidium iodide. Observation was carried out with confocal LEICA TCS 4D microscope equipped with argon/krypton laser.

For the analysis of the tissutal antigen expression distal colon mucosa samples from DMH treated and not treated BDIX rats were fixed with buffered formalin and paraffin embedded. Histological sections were immunolabeled using anti-RTQ monoclonal antibody (1:10 diluted) and the reaction was detected with peroxidase conjugated secondary antibodies using DAKO Cytomation LSAB 2® System HRP (Liquid DABN) kit.

Preclinical Used Models

For in vivo preclinical model male BDIX strain, alotane anesthetized, administered intramuscularly five times at 7 days intervals with 20 mg/kg of 1,2-dimethyl hydrazine hydrochloride (DMH) rats were used. At the tumor occurrence animals were sacrificed and distal colon mucosa was sampled for immunohistochemical analysis of the antigen expression.

As in vitro preclinical model DHD/K12 line cells, originally obtained from BDIX strain rats by treatment with dimethyl hydrazine hydrochloride were used.
Flux Cytometry To verify the antigen expression in DHD-K12 cells by cytofluorimetric analysis the cells were detached with trypsin/EDTA, labeled with anti-RTQ (1:20 diluted) monoclonal antibody and analyzed cytofluorometrically (FACscan Becton-Dickinson).

Immunolabeling was carried out using both non fixed cells, to detect the antigen expression only on cellular membrane, and paraformaldehyde fixed, Triton-X 100 permeabilized cells to detect cytoplasmic expression thereof.
Results Immunoblotting was carried out using anti-RTNKEASI (anti-RTN) monoclonal antibody against RTNKEASI and RTQKEASI (SEQ ID NO:2) sequences. Result reported in FIG. 5 shows the reaction of anti-RTN polyclonal antibody with RTNKEASI (lane 1) and also with RTQKEASI (SEQ ID NO:2) (lane 3) peptides.

Immunofluorescence and fluorescence microscopy analyses allowed to detect immunopositivity of DHD-K12 cells for anti-RTQ monoclonal antibody. Results obtained using anti-RTQKEASI (SEQ ID NO:2) monoclonal antibody show exclusively cytoplasmic but not membrane positivity of DHD-K12 cells; anti-RTN polyclonal antibody gave also membrane positivity (FIG. 6).

Further from indirect immunofluorescence analysis using anti-RTQ monoclonal antibody it was detected that DHD-K12 cells show intracellular antigen distribution superimposable to that previously obtained with the use of anti-RTN polyclonal antibody, but more specific with respect to the latter as shown in FIG. 7. FIG. 7 shows the prevalently cytoplasmic DHD-K12 cell positivity against anti-RTQ monoclonal antibody with a vesicular distribution pattern, accumulation in a few cells in the perinuclear area (Golgi and lysosomes) and many cells in the nuclear area.

Finally immunohistochemical analysis carried out for normal and DMH treated BDIX rat colon tissue allowed to verify the immunopositivity for anti-RTQ monoclonal antibody (sampling carried out at $11^{th}$ (DMH6) and $26^{th}$ (DMH20) weeks after last DMH dose). While the result for normal colon mucosa tissue was negative, the tissue from DMH treated rats showed specific immunopositivity whose intensity and distribution increased with tumor progression (FIG. 8). Particularly FIG. 8 shows that while RTQ antigen is not expressed in the normal colon mucosa it is expressed already at $11^{th}$ week after DMH last dose both in mucosa epithelial cells towards intestinal lumen and tumoral and interstitial cells in the mucosal crypts. This positivity increases at $26^{th}$ week after DMH last dose. Intracellular distribution is mainly cytoplasmic but nuclear also in several cells. Anti-RTN and anti-RTQ tissutal distributions are similar, but the latter is much more specific.

EXAMPLE 5

Therapeutic Vaccination by Immunization with a DNA in Inbred BDIX Rats

Materials and Methods

DHD/K12 tumoral cells ($2 \times 10^6$ in 0.5 ml/animal) were injected subcutaneously (s.c.) in the cervical region of BDIX rats at the beginning of the experiment (T0).

Next day the experimental group (DNA vax, n=8) was vaccinated with 200 µg/animal of a DNA pRC11Fz vaccine, administered by i.m. injection in front tibial muscle using an insulin syringe and 29½ gauge needle (Becton Dickinson, Ref. No. 324804 microfine). After three weeks "DNA vax" group was subjected to a immunization booster dose by electroporation (BTX ECM 830, 100 volts/cm, 20 ms, 1 Hz electroporator) in quadriceps muscles with 200 µg/limb of a DNA pRC11Fz vaccine. Electroporation was carried out under zoletil and xilor general anesthesia. Control group (n=8) at the beginning of the experiment (T0) was subjected to subcutaneous (s.c) inoculum of DHD/K12 tumoral cells ($2\times10^6$ in 0.5 ml/animal) in the cervical retronuchal region of BDIX rats. After a week FCA adjuvant (600 µl Freund's Complete Adjuvant) and equal volume of 1% BSA in PBS (1.2 ml/animal) were administered intradermally to the animals in six loci (0.2 ml/locus). Treatment was repeated weekly seven times.

BDIX rats vaccination after a 9 week growth of colon carcinoma DHD-K12 syngenic cells was carried out both with RTQKEASI (SEQ ID NO:2) containing a DNA vaccine (DNA vax) (2 treatments in the $1^{st}$ and $4^{th}$ weeks) according to the invention and control (Freund's adjuvant; 7 treatments every week).

Results

FIG. 9 shows the results of therapeutical immunization with a DNA vaccine of consanguineous BDIX rats after a 9 week growth of colon carcinoma DHD-K12 syngenic cells indicating the effect on the tumor growth (tumor volume).

Table 3 indicates values obtained after the treatment with a DNA vaccine (DNA vax) and control with reference to tumor volume and survival percentage.

TABLE 3

|  | Control | DNA vaccine |
|---|---|---|
| Tumor volume mean ± DS | 3.33 ± 1.88 | 1.15 ± 0.91 |
| Volume interval | 1.5-6.5 | 0.15-2.5 |
| Survival/total (%) | 6/8 (75) | 8/8 (100) | p value: 0.00556

BIBLIOGRAPHY

Ferlay J, Bray F, Sankila R, Parkin D M. IARC Cancer Base No. 4; 1999
Parkin D M, Whelan S L, Ferlay J, Teppo L, Thomas D B. IARC Scient. Publ. No. 155; 2002
Ferlay J, Bray F, Pisani P, Parkin D M. IARC Cancer Base No. 5; 2001
W. Yan, N. Sheng, M. Seto, J. Morser, Q. Wu. *J. Biol. Chem.* 274: 14926-14935, 1999
F. Wu, Q. Wu. *Cancer Res.* 63: 8318-8322, 2003
Holcombe R F, Marsh J L, Waterman M L, Lin F, Milovanovic T, Truong T. *Mol Pathol.* 55(4):220-6, 2002.
WO 01/62786
WO-A-001458
WO 03/045997

The invention claimed is:

1. An expression vector comprising:

an isolated DNA sequence encoding for an immunogenic peptide comprising QKEASI (SEQ ID No: 1) sequence belonging to the region from cysteine 2 to cysteine 3 of the mammalian Corin protein Frizzled2 domain, said peptide having a length from 8 to 12 amino acids; and the sequence encoding for an immunomodulating compound selected from the group consisting of immunomodulating chemokines and cytokines.

2. The expression vector according to claim 1 wherein said chemokines and cytokines are selected from the group consisting of IL-12, IL-2, INF-gamma, and GM-CSF.

3. A method for reducing the occurrence of tumors in a subject carrying at least one HLA allele selected from the group consisting of HLA-A0201, HLA-A03, HLA-B0702, HLA-B2705 and HLA-B5101, comprising administering to said subject a composition comprising an immunogenic peptide comprising QKEASI (SEQ ID No: 1) sequence belonging to the region from cysteine 2 to cysteine 3 of the mammalian Corin protein Frizzled2 domain, said peptide having a length from 8 to 12 amino acids or an expression vector comprising an isolated DNA sequence encoding for said peptide.

4. The method according to claim 3, wherein the tumor is colon rectal carcinoma.

5. The method according claim 3; wherein the composition is administered in association at least with a chemotherapeutic agent.

* * * * *